United States Patent [19]

Frater et al.

[11] Patent Number: 4,687,849
[45] Date of Patent: Aug. 18, 1987

[54] [(ISOPROPYLIDENEAMINO)OXY]-ETHYL-2-[[6-CHLOROQUINOXALINYL)OXY]-PHENOXY]PROPIONATE POSTEMERGENT HERBICIDE

[75] Inventors: Georg Frater, Greifensee; Milos Suchy, Pfaffhausen; Jean Wenger, Uster; Paul Winternitz, Greifensee, all of Switzerland

[73] Assignee: Hoffmann-La Roche Inc., Nutley, N.J.

[21] Appl. No.: 784,067

[22] Filed: Oct. 4, 1985

[51] Int. Cl.[4] .................... C07D 241/44; A01N 43/60
[52] U.S. Cl. ................................................. 544/354
[58] Field of Search ......................................... 544/354

[56] References Cited

U.S. PATENT DOCUMENTS 4,435,207  3/1984  Frater ...................................... 71/92
4,545,807  10/1985  Frater .................................... 544/354

Primary Examiner—Mark L. Berch
Attorney, Agent, or Firm—Jon S. Saxe; George M. Gould; Dennis P. Tramaloni

[57] ABSTRACT

The oxime ester compound [(isopropylideneamino)oxy]-ethyl-2-[[(6-chloroquinoxalinyl)oxy]phenoxy]propionate, processes for the preparation thereof, herbicidal compositions containing said compound and methods of use of the composition.

2 Claims, No Drawings

[(ISOPROPYLIDENEAMINO)OXY]-ETHYL-2-[[6-CHLOROQUINOXALINYL)OXY]PHENOXY]PROPIONATE POSTEMERGENT HERBICIDE

SUMMARY OF THE INVENTION

The invention relates to the oxime ester compound, [(isopropylideneamino)oxy]-ethyl-2-[[(6-chloroquinoxalinyl)oxy]phenoxy]propionate of the formula I:

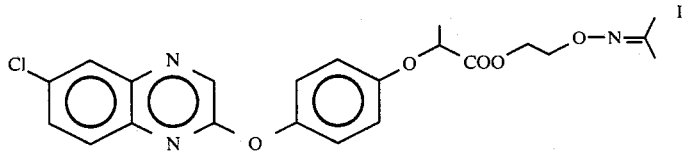

In another aspect, the invention relates to herbicidal composition, methods of use and processes for prepare the compound of formula I.

DETAILED DESCDRIPTION OF THE INVENTION

The invention is directed to the oxime ester compound, [(isopropylideneamino)oxy]-ethyl-2-[[(6-chloroquinoxalinyl)oxy]phenoxy]propionate of the formula I:

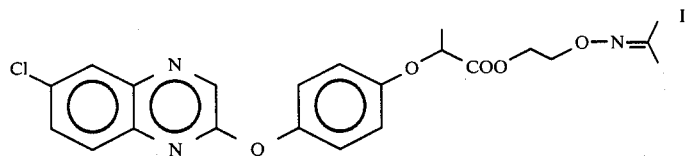

The invention is also directed to processes for the preparation of the compound of formula I as well as herbicidal compositions which contain, as the active ingredient, the compound of formula I, and methods for its use. The compound exhibits excellent post-emergence herbicidal activity.

The compound of formula I can be prepared by one of the procedures described below.

A. Reacting a compound of the general formula:

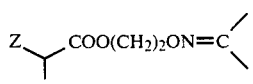

wherein Z is a leaving group, with a compound of the formula

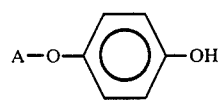

wherein A is 6-chloro-2-quinoxalinyl, or an alkali metal salt thereof.

In formulas II and III above, Z represents a leaving group, especially chlorine, bromine, iodine, mesyloxy and tosyloxy. The leaving group may also be a reactive hydroxy group, especially a hydroxy group activated by reaction with triphenylphosphine and azodicarboxylic acid or an ester thereof especially diethyl azodicarboxylate [see for example Bull. Chem. Soc. Japan 46, 2833 (1973) or Angew. Chem. 88, 111(1976)].

In accordance with this procedure, a compound of formula II is reacted with a compound of formula III or an alkali metal salt thereof in a manner known per se, and if required in the presence of a base. The reaction is conveniently carried out in an inert organic solvent such as hydrocarbon, for example, benzene, toluene, or the like, an ether, for example diethyl ether, tetrahydrofuran, dimethoxyethane, or hexamethylphosphoric acid triamide or the like. The temperature and pressure are not critical and the reaction is preferably carried out at a temperature between −20-C. and the reflux temperature of the reaction mixture, preferably between −10 and 60-C.

B. Reacting a compound of the formula

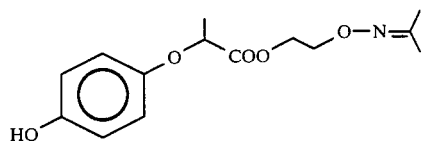

with 2,6-dichloroquinoxaline.

In accordance with this procedure, the compound of this formula is reacted with 2,6-dichloroquinoxaline in a organic inert organic solvent, such as dimethylformamide, dimethylsulfoxide, acetonitrile, acetone, etc., in the presence of a base such as potassium carbonate. The temperature and pressure are not critical and the reaction is carried out at an elevated temperature, e.g. between ea. 40 and 80-C., preferably around 65-C.

Since the oxime ester compound of formula I has an asymmetric carbon atom in the a-position to the carbonyl group, this compound can exist in optically active isomeric forms. In fact, these esters can have more than one asymmetric carbon atom. The racemic compound can be resolved in their dextrorotatory and laevorotatory isomers using known procedures as, for example, that described in Industrial and Engineering Chemistry 60(8), 12–28 (1968). The racemic mixture as well as the isomers all have herbicidal activity with the D-isomer having the highest activity followed by the racemic mixture and the L-isomer.

The isomers especially the D-isomer can also be prepared by synthesis from corresponding optically active starting materials.

This invention is also directed to herbicidal compositions which comprise inert carrier material and, as the active ingredient, the compound of formula I. These herbicidal compositions suitably contain, as the inert carrier material, at least one of the following ingredients: carrier materials, wetting agents, inert diluents and solvents.

The compound of formula I is practically water-insoluble. Thus, the usual methods of formulation of insoluble materials can be followed. For example, the compounds can be dissolved in a water-immiscible solvent such as a high-boiling hydrocarbon which conveniently contains dissolved emulsifiers so that the solution acts as a self-emulsifiable oil when added to water.

The compound of formula I can also be mixed with a wetting agent, with or without an inert diluent, to form a wettable powder which is soluble or dispersible in water. The compounds can alternatively be mixed with an inert diluent to form a solid or pulverulent product.

Suitable inert diluents are solid inert media including pulverulent or finely divided solids such as clays, sand, talc, mica, fertilizers and the like. The resulting compositions can be either dusts or materials of relatively large particle size.

Wetting agents, suitable for use with the compounds of this invention, can be anionic, cationic or nonionic.

Examples of anionic wetting agents include soaps, fatty sulfate esters such as dodecyl sodium sulfate, octadecyl sodium sulfate and cetyl sodium sulfate, fatty aromatic sulfonates such as alkylbenzene-sulfonates and butylnaphthalene-sulfonates, and the more complex fatty sulfonates such as the amide condensation products of oleic acid and N-methyltaurine or the sodium sulfonate of dioctyl succinate.

Examples of cationic wetting agents include cetyl-trimethylammonium bromide and the like.

Examples of nonionic wetting agents include, for example, condensation products of fatty acids, fatty alcohols or fatty substituted phenols with ethylene oxides; fatty acid esters and ethers of sugars or polyhydric alcohols; condensation products of sugars or polyhydric alcohols with ethylene oxide; and block copolymers of ethylene oxide and propylene oxide.

The herbicidal compositions of this invention can also be used in aerosol form using, in addition to the propellant gas, carrier material comprising a co-solvent and a wetting agent. Suitable propellant gases include the polyhalogenated alkanes such as dichlorodifluoromethane.

The herbicidal compositions of this invention can also contain other active ingredients such as synergistic agents, insecticides, bactericides, other herbicides, fungicides, plant growth regulators and fertilizers. Such combination preparations are suitable for increasing the activity or for broadening the spectrum of activity.

The compound of formula I is useful as a postemergent herbicide. It is particularly suitable in combatting weed grasses such as, e.g.

| Annual Grasses | |
| --- | --- |
| wild oats | *Avena fatua* |
| broadleaf signalgrass | *Brachiaria platyphylla* |
| sandspur | *Cenchrus* spp. |
| crabgrass | *Digitaria* spp. |
| barnyardgrass | *Echinochloa crusgalli* |
| goosegrass | *Eleusine indica* |
| fall panicum | *Panicum dichotomiflorum* |
| itchgrass | *Rottboellia exaltata* |
| foxtails | *Setaria* spp. |
| shattercane | *Sorghum bicolor* |
| Texas panicum | *Panicum texacum* |
| crowfootgrass | *Dactyloctenium aegyptium* |
| junglerice | *Echinochloa column* |
| sprangletop | *Leptochloa* sp. |
| volunteer sorghum | *Sorghum bicolor* |
| volunteer wheat | *Triticum aestivum* |
| volunteer barley | *Hordeum vulgare* |
| volunteer corn | *Zea mays* |
| Perennial grasses | |
| quackgrass | *Agropyron repens* |
| bermudagrass | *Cynodon dactylon* |
| johnsongrass | *Sorghum halepense* |

The compound is suitable for use against these weed grasses especially in soybeans, cotton, peanuts, grape, sugar beets, potatoes and vegetable crops.

In general, the compounds of this invention are effective as herbicides when applied at a concentration of about 0.01 to about 6 kg/ha with the preferred concentration range being from about 0.03 to about 0.3 kg/ha. An especially preferred application rate is from about 0.06 to about 0.18 kg/ha.

The herbicidal compositions of this invention can be in the form of concentrates suitable for storage or shipment. Such compositions can contain, e.g. from about 2% to about 90% by weight, based on the weight of the total composition, of one or more of the active compounds of this invention. These concentrates can be diluted, with the same or different inert carrier material, to concentrations which are suitable for actual use. Ready-to-use compositions can contain concentrations of from 2% to 80% by weight of the active ingredient. Particularly preferred concentrations of active ingredients in the herbicidal compositions of this invention are from about 2% to about 80% by weight and preferably from about 50% to about 80% by weight.

The following Examples illustrate the present invention:

EXAMPLE 1

Step 1:

109 g ethylene oxide are introduced into a 2.5 l reaction vessel, equipped with agitator, thermometer and cooling device, contain 190 g acetone oxime, 2 g calcium hydroxide and 380 ml of water at room temperature with stirring, the reaction temperature being held at 30°–35° C.

An additional quantity of 41 g ethylene oxide is introduced after a reaction time of 90 minutes, the reaction mixture being stirred for another 20 hours, whereupon the solution is saturated with sodium chloride and extracted 4 times with 400 ml ether each.

The united ether extracts are dried over sodium sulfate and concentrated. The crude 2-[(isopropylideneamino)oxy]ethanol obtained in this step 1 is purified by distillation.

Step 2:

In a 2 l reaction vessel equipped with agitator, water separator, cooling device and thermometer, 148 g calcium lactate are dissolved in 750 ml benzene, the mixture being stirred for 30 minutes, whereupon 295 g of 2-[(isopropylideneamino)oxy]ethanol obtained in step 1, are added to the mixture. By adding 65 ml concentrated sulfuric acid within 30 minutes, calcium sulfate is precipitated.

The reaction mixture is heated to reflux temperature, whereby water is separated until complete removal of the water.

Heating on reflux is continued over night, whereupon the mixture is cooled and 10 g silica gel and 0.5 g activated carbon are added. The filtrate obtained after stirring and filtration is washed twice with 50 ml saturated sodium bicarbonate solution and one with 50 ml saturated sodium chloride.

The united aqueous phases are extracted twice with 50 ml ethyl acetate each.

The united organic phases are dried over 50 g sodium sulfate and concentrated. The resulting residue contains about 55% 2-[(isopropylideneamino)oxy]-ethyl-L(−)-lactate.

This residue is distilled under reduced pressure. The resulting 98% pure product (2-[(isopropylideneamino)oxy]-ethyl-L(−)-lactate (117 g) has an optical rotation of $[\alpha]_D^{20} = -8,68$ in chloroform (c=1.11%).

Step 3:

50 g of the product obtained in step 2,2-[(isopropylideneamino)oxy]-ethyl-L(−)-lactate, are dissolved in a 500 ml reaction vessel, equipped with agitator and thermometer, in 26 ml methylene chloride, whereupon 50 g toluene sulfonylchloride are added in portions.

The resulting clear solution is cooled to 0° C., whereupon 92 ml triethylamine are added within 1 hour in such a manner that the temperature does not exceed 5° C.

After stirring for 6 hours at 0°–5° C. the reaction mixture is allowed to stand at room temperature over night, whereupon the reaction is completed.

75 ml water are added to the reaction mixture at 10° C., whereupon the pH is adjusted to 2–3 by adding about 8 ml of concentrated hydrochloric acid.

The lower yellowish organic phase is separated and washed twice with 50 ml water each.

The combined aqueous phase are extracted twice with 50 ml methylene chloride each.

The organic phases are combined, dried over sodium sulfate, treated with activated carbon, concentrated under reduced pressure and dried at 40° C.

The resulting product, 2-[(isopropylideneamino)oxy]-ethyl-L(−)-2-(toxyloxy)-propionate (84.9 g), has an optical rotation of $[\alpha]_D^{20} = 27,49°$ in chloroform (c=1,031%) −34,33° in ethanol (c=1,101%); $n_D^{20} = 1,5042$; density 1,10.

Step 4:

13.6 g 4-[(6-chloroquinoxalinyl)oxy]phenol in 100 ml toluene are added dropwise to a suspension of 4 g lithium hydride in 20 ml toluene. After hydrogen evolution has ceased, 100 ml dimethyl sulfoxide are added and the toluene is distilled off.

The resulting reaction mixture is treated with 17,15 g 2-[(isopropylideneamino)]-ethyl-L-(−)-2-(tosyloxy)-propionate, the product of step 3, and stirred for 7 hours at 25°–30° C.

The reaction mixture is then poured in 200 ml of water, extracted with 200 ml tert.butyl methyl ether, whereupon the organic solvent is evaporated.

The resulting product, [(isopropylideneamino)oxy]-ethyl-D-2-[[(6-chlorochinoxalinyl)oxy]phenoxy]propionate, is crystallized from isopropanol; m.p.=65°–66° C.; $[\alpha]_D^{22} = +27,2°$ (in chloroform).

EXAMPLE 2

Step 1:

124.1 g of the monoethylether of hydroquinone in 200 ml of dimethylformamide are added to a solution of 24 g sodium hydride in 100 ml of dimethylformamide.

The reaction is exothermal under hydrogen evolution. The reaction mixture is stirred for 1 hour, whereupon 0.44 g 1,4,7,10,13-pentaoxycyclopentadecane are added, whereupon 272.3 g L-(2)-(tosyloxy)propionic acid ethylester, dissolved in 200 ml of dimethylformamide, are added dropwise. The temperature is allowed to rise to about 50° C., the solution becoming reddish.

After 2 hours the reaction mixture is poured into 2.5 l water and extracted 3 times with ether. The ether phase is extracted twice with 2n sodium hydroxyde, washed neutral with water and dried over sodium sulfate, whereupon the solvent is evaporated.

The resulting residue (210.3 g) is distilled, whereby 176 g of ethyl D-2-[4-methoxyphenoxy]propionate are obtained; b.p. 0,06—92°–96° C.

Step 2:

143.55 g of the product of step 1 are dissolved in 200 ml of methanol, 69 ml of Claisen reagent (obtained by dissolving 35 g of potassium hydroxyde in 25 ml of water, followed by addition of 100 ml of methanol and cooling) are added dropwise to the resulting solution, whereupon the reaction mixture is stirred until the pH is neutral.

The reaction mixture is then poured into water, acidified with 2n hydrochloric acid and extracted twice with ethyl acetate. The united ethyl acetate phases are washed neutral and concentrated, whereupon the resulting residue is crystallized from ethyl acetate/hexane. The filtrate obtained from crystallization is concentrated and the resulting residue is crystallized from a mixture of ethylene chloride/hexane, whereby 34.7 g of D-2-[4-methoxyphenoxy]propionic acid are obtained: m.p. 60°–62° C.; $[\alpha]_D^{22} = +19,813°$ in chloroform.

Step 3:

71.5 ml thionychloride are added dropwise to 29.4 g of D-2-[4-methoxyophenoxy]propionic acid, whereupon the mixture is heated to reflux.

The reaction is completed after 2 hours, whereupon the access thionychloride is distilled off under reduced pressure.

The oily residue is D-2-[4-methoxyphenoxy]propionylchloride, which is used without further purification in the next step.

Step 4:

16.1 g D-2-[4-methoxyphenoxy]propionylchloride are dissolved in 75 methylene chloride. The resulting solution is cooled to 0° C., whereupon a solution of 11.0 g 2-[(isopropylideneamino)oxy]-ethanol and 8.9 g pyridine, dissolved in 25 methylene chloride, is added to the above solution in such a manner that the temperature does not exceed 5° C.

The reaction mixture is then stirred for 10 minutes, whereupon it is poured into 200 ml ice water.

The methylene chloride phase is washed with 100 ml of a 5% sodiumhydrogencarbonate solution and 100 ml of water, dried over sodium sulphate, whereupon the solvent is evaporated.

For purifying the product, it is chromatographed on a 10 fold quantity of silica gel with n-hexan/ethyl acetate (8:2).

The resulting product (18.2 g) is [(isopropylideneamino)oxy]-ethyl-D-2-(4-methoxyphenoxy)propionate, a colorless oil; $[\alpha]_D^{22} = +29.81°$ (c=0.962% in chloroform).

Step 5:

A solution of 14 g [(isopropylideneamino)oxy]ethyl-D-2-[4-methoxyphenoxy]propionate and 18.5 g sodium iodide in 200 ml of acetonitrile is heated to 60° C.

13.4 g trimethylchlorosilane are added to this solution within 1 hour, whereupon the resulting mixture is heated to 60° C.

13.4 g trimethylchlorosilane are added to this solution within 1 hour, whereupon the resulting mixture is heated to 60° C. over night.

The reaction mixture is poured into 500 ml of ice water and extracted twice with 150 ml ether. The united ether phases are washed with 100 ml of a 5% sodiumhydrogencarbonate solution and 100 ml of water, dried over sodium sulfate and concentrated.

The resulting raw product is chromatographed on a 10 fold quantity of silica gel with hexane/ethyl acetate (8:2).

The resulting colorless oil is [(isopropylideneamino)oxy]ethyl-D-2-[4-hydroxyphenoxy]-propionate.

Step 6:

2.96 g [(isopropylideneamino)oxy]ethyl-D-2-[4-hydroxyphenoxy]propionate, 2.0 g 2.6-dichloroquinoxaline and 2.8 g potassium carbonate are dissolved in 20 ml of dimethylformamide.

The reaction mixture is stirred at 65° C. for 3 hours, poured into 100 ml of a 5% sodium chloride solution and extracted with 50 ml of ethyl acetate.

The organic phase is dried over sodium sulphate, treated with activated carbon, concentrated to about 10 ml and treated with 10 ml of hot n-hexane. The product, [(isopropylideneamino)oxy]-ethyl-D-2-][(6-chloroquinoxalinyl)oxy]phenoxy]propionate, is obtained on crystallization; $[\alpha]_D^{22} = 26,9°$ in chloroform; m.p. = 62°–64° C.

EXAMPLE 3

4.4 g of a 55% dispersion of sodium hydride in mineral oil are added with stirring at room temperature to a solution of 27,26 g of p-[(6-chloro-2-quinoxalinyl)oxy]phenol in 100 ml of absolute dimethylformamide. Stirring is continued for 1 hour at room temperature, whereupon 0,26 g of 1,4,7,10,13-pentaoxycyclopentadecane and a solution of 34,34 g L-2-[(isopropylideneamino)oxy]ethyl-2-[(p-toluenesulphonyl)oxy]propionate in 10 ml absolute dimethylformamide are added with stirring. Stirring is continued for 2 hours at 60°–70° C. 1000 ml of water are added to the cooled reaction mixture and the mixture is then extracted 3 times with 200 ml ether each. The ether phases are washed to neutral, dried over sodium sulfate and evaporated to dryness under reduced pressure. The residue is purified by chromatography on an alumina column with ether/hexane (1:1). The product is recrystallized from ether/hexane, whereby 2-[(isopropylideneamino)oxy]ethyl D-2-[p-[(6-chloro-2-quinoxalinyl)oxy]-phenoxy]propionate is obtained; m.p. 62°–64° C.; $[\alpha]_D^{20} + 29,3°$ (CHCl$_3$; c=0,10%).

EXAMPLE 4

8.7 g pyridine in 10 ml dichloromethane are added to a solution of 36,32 g D-2-[p-[(6-chloro-2-quinoxalinyl)oxy]phenoxy]propionic acid chloride and of 11,71 g 2-[(isopropylideneamino)oxy]ethanol in 100 ml dichloromethane at 0° C. with stirring. Stirring is continued for 1 hour at room temperature, whereafter the solvent is distilled off and the residue is dissolved in 100 ml ether and thoroughly washed with water. The solution is dried over sodium sulphate and evaporated to dryness under reduced pressure.

The resulting material is purified by chromatography on a silica gel column with ether/hexane (1:1). The pure fractions are recrystallized from ether/hexane, whereby 2-[(isopropylideneamino)oxy]ethyl D-2-[p-[(6-chloro-2-quinoxalinyl)oxy]phenoxy]proprionate is obtained; m.p. 62°–64° C., $[\alpha]_D^{20} + 29,7°$ (CHCl$_3$; c=0.93%).

EXAMPLE 5

An emulsifiable concentrate is prepared by mixing the following ingredients with one another:

| | |
|---|---|
| Compound of formula I | 500 g |
| Condensation product of an alkylphenol and ethylene oxide; calcium dodecylbenzenesulphonic acid | 100 g |
| Epoxidated soya oil with an oxirane oxygen content of about 6% | 25 g |
| Butylated hydroxytoluene | 10 g |

The mixture is made up to 1 liter with xylene.

What is claimed is:

1. The compound [(isopropylideneamino)oxy]-ethyl-2-[[(6-chloroquinoxalinyl)oxy]phenoxy]propionate.

2. The D-isomer of the compound of claim 1.

* * * * *

Disclaimer 4,687,849.—*Georg Frater*, Greifensee; *Milos Suchy*, Pfaffhausen; *Jean Wenger*, Uster; *Paul Winternitz*, Greifensee, all of Switzerland. [(ISOPROPYLIDENEAMINO)OXY]-ETHYL-2-[[6-CHLOROQUINOXALINYL)OXY]-PHENOXY]-PROPIONATE POSTEMERGENT HERBICIDE. Patent dated Aug. 18,1987. Disclaimer filed May 15, 1989, by the assignee, Hoffman-La Roche, Inc.

Hereby enters this disclaimer to the entire term of said patent.
[ *Official Gazette July 25, 1989* ]